(12) United States Patent
Curran et al.

(10) Patent No.: US 6,825,043 B1
(45) Date of Patent: Nov. 30, 2004

(54) FLUOROUS TAGGING COMPOUNDS AND METHODS OF INCREASING THE FLUOROUS NATURE OF COMPOUNDS

(75) Inventors: Dennis P. Curran, Pittsburgh, PA (US); Roger Read, Kensington (AU); Zhiyong Luo, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/565,087

(22) Filed: May 5, 2000

(51) Int. Cl.[7] .................. G01N 37/00; G01N 33/00; C07C 19/08; C07C 17/26; C07C 17/38
(52) U.S. Cl. .................. 436/56; 436/124; 570/142; 570/171; 570/177
(58) Field of Search .................. 546/245; 436/56, 436/124; 570/142, 171, 177

(56) References Cited

U.S. PATENT DOCUMENTS

| | | |
|---|---|---|
| 3,627,799 A | 12/1971 | Anderson |
| 3,732,274 A | 5/1973 | Fox |
| 4,454,233 A | 6/1984 | Wang |
| 5,401,847 A | 3/1995 | Glazer |
| 5,463,082 A | 10/1995 | Horvath |
| 5,777,121 A | 7/1998 | Curran |
| 5,798,032 A | 8/1998 | Khan |
| 5,859,247 A | 1/1999 | Curran |
| 6,156,896 A | 12/2000 | Curran |

FOREIGN PATENT DOCUMENTS

| | | |
|---|---|---|
| GB | 1 149 280 | 4/1969 |
| WO | WO 91/07381 | 5/1991 |
| WO | WO 01/85675 A3 | 11/2001 |

OTHER PUBLICATIONS

Jiang et al. J. Chem. Soc. Commun., 1986, pp. 745–746.*
McMurry, John "Organic Chemistry" (1996) Brooks/Cole Publishing, pp. 375–384.*
Curran, D. P.; Luo, Z. Y. Fluorous synthesis with fewer fluorines (light fluorous synthesis): Separation of tagged from untagged products by solid–phase extraction with fluorous reverse–phase silica gel. J. Am. Chem. Soc., vol. 121, 1999, 9069–9072.
Curran, D. P.; Hadida, S.; He, M. Thermal allylations of aldehydes with a fluorous allylstannane. Separation of organic and fluorous products by solid phase extraction with fluorous reverse phase silica gel. J. Org. Chem. 1997, 62, 6714–6715.
Curran, D. P. Strategy–level separations in organic synthesis: From planning to practice. Angew. Chem., Int. Ed. Eng. 1998, 37, 1175–1196.
Curran, D. P.; Ferritto, R.; Hua, Y. Preparation of a fluorous benzyl protecting group and its use in a fluorous synthesis approach to a disaccharide. Tetrahedron Ltt. 1998, 39, 4937–4940.
Danielson, N. D.; Beaver, L. G.; Wangsa, J. Fluoropolymers and fluorocarbon bonded phases as column packings for liquid chromatography. J. Chromat. 1991, 544, 187–199.
Kainz, S.; Luo, Z. Y.; Curran, D. P.; Leitner, W. Synthesis of perfluoroalkyl–substituted aryl bromides and their purification over fluorous reverse phase silica. Synthesis 1998, 1425–1427.
Studer, A.; Hadida, S.; Ferritto, R.; Kim, S. Y.; Jeger, P. et al. Fluorous synthesis: A fluorous–phase strategy for improving separation efficiency in organic synthesis. Science vol. 275, 1997, 823–826.
Studer, A.; Curran, D. P. A strategic alternative to solid phase synthesis: Preparation of a small isoxazoline library by "fluorous synthesis". Tetrahedron 1997, 53, 6681–6696.
Studer, A.; Jeger, P.; Wipf, P.; Curran, D. P. Fluorous synthesis: Fluorous protocols for the ugi and biginelli multicomponent condensations. J. Org. Chem. 1997, 62, 2917–2924.
Takeuchi, S.; Nakamura, Y.; Ohgo, Y.; Curran, D. P. Catalytic enantioselective protonation of a samarium enolate with fluorous chiral and achiral proton sources in fluorous biphasic systems. Tetrahedron Lett. 1998, 39, 8691–8694.
Hudlicky M. New synthesis and reactions of perfluoro–tert–butyl chloroformate. Journal of Fluorine Chemistry, Elsevier Sequola, Lausanne, CH, vol. 20, 1982, pp. 649–658, XP001011888. ISSN: 0022–1139.

* cited by examiner

*Primary Examiner*—Padmashri Ponnaluri
*Assistant Examiner*—My Chau T Tran
(74) *Attorney, Agent, or Firm*—Bartony & Hare, LLP

(57) ABSTRACT

A method of increasing the fluorous nature of a compound includes the step of reacting the compound with at least one second compound having the formula:

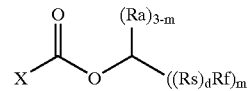

wherein Rf is a fluorous group, Rs is a spacer group, d is 1 or 0, m is 1, 2 or 3, Ra is an alkyl group and X is a suitable leaving group. A compound has the formula:

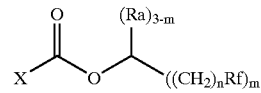

wherein Rf is a fluorous group, n is an integer between 0 and 6, m is 1, 2 or 3, Ra is an alkyl group and X is a leaving group.

7 Claims, 9 Drawing Sheets

*Preparation of alcohols*

M = Mg or Li; X = Cl or OR'; n = 2 or 3; Rf = $C_nF_{2n+1}$

*Preparation of Boc reagents and reaction with amines*

Fluorous Boc protected derivatives

Examples of $^F$Boc protection

Similarly prepared from the corresponding amino acidds 12b-c

Examples of amide formation

Structures of amines 14a'-d'

Yields of products 15

| 14 \ 13 | a | b | c | d |
|---|---|---|---|---|
| a' | 71 | 82 | 21 | quan. |
| b' | 44 | 98 | 88 | 81 |
| c' | 37 | 23 | 94 | 59 |
| d' | 31 | 77 | 73 | 87 |

Products generated by deprotection of the fluorous Boc protected amides with HCl/MeOH from 15aa' 92% from 15bb' 100% from 15cc' 53% from 15dd' 86%

Yields determined by $^1$H NMR spectroscopy with the corresponding hydrochloride salts.

|     | Rf        | n |
|-----|-----------|---|
| 16a | $C_6F_{13}$ | 0 |
| 16b | $C_6F_{13}$ | 1 |
| 16c | $C_4F_9$    | 1 |

HPLC retention times on a Fluofix column

| Compound | retention time (min)[a] |
|----------|-------------------------|
| 9        | 22.5                    |
| 16a      | 33.8                    |
| 16b      | 33.4                    |
| 16c      | 24.1                    | a) HPLC method: MeOH:H$_2$O (4:1), 30 min gradient to 100% MeOH, 10 min gradient to MeOH:THF (9:1)

Diversity reagents 17{1-8}

Diversity reagents 20{1-12}

Figure 9.

|  | 19{1} | 19{2} | 19{3} | 19{4} | 19{5} | 19{6} | 19{7} | 19{8} |
|---|---|---|---|---|---|---|---|---|
| 20{1} | (70) | quan. | 94 | quan. | 89 | 95 | 5 | 60 |
| 20{2} | 71 | (80) | 84 | 80 | 61 | 70 | 48 | 48 |
| 20{3} | 48 | 58 | 0 | 65 | 10 | 41 | (30) | 28 |
| 20{4} | (46) | 62 | 85 | (50) | 50 | 43 | 36 | 32 |
| 20{5} | 56 | 72 | 68 | 52 | (48) | 47 | 41 | 41 |
| 20{6} | 12 | 9 | 10 | 10 | 0 | 9 | 0 | (9) |
| 20{7} | 51 | 63 | (71) | 54 | 51 | 60 | 0 | 36 |
| 20{8} | 72 | 82 | 83 | 94 | 81 | 82 | 5 | 56 |
| 20{9} | 13 | (18) | 17 | 10 | 0 | 14 | 0 | 11 |
| 20{10} | 61 | 77 | 68 | 81 | 52 | (71) | 11 | 40 |
| 20{11} | 49 | 63 | 62 | 49 | (44) | 45 | 5 | 32 |
| 20{12} | 27 | 38 | 31 | 32 | 0 | 25 | 14 | (14) |

All compounds were characterized by LCMS. Compounds with yields in parentheses were also characterized by proton NMR spectroscopy.

FLUOROUS TAGGING COMPOUNDS AND METHODS OF INCREASING THE FLUOROUS NATURE OF COMPOUNDS

FIELD OF THE INVENTION

The present invention relates to fluorous tagging compounds and to methods of increasing the fluorous nature of compounds.

BACKGROUND OF THE INVENTION

Organic chemists are typically trained that organic compounds have to be synthesized, as pure substances through well-planned reactions and scrupulous separation. In fields such as drug discovery, catalyst design and new material development, however, tens of thousands of organic compounds must be synthesized and tested to discover a few active ones. In the pharmaceutical industry, for example, synthesizing such a large number of compounds in the traditional way is too slow compared to the rapid emergence of new biological targets. A major factor limiting the productivity of orthodox solution (liquid) phase organic synthesis is the tedious separation process for the purification of products. High throughput organic synthesis, therefore, preferably integrates organic reactions with rapid purification/separation procedures.

Recently, fluorous synthetic and separation techniques have attracted the interest of organic chemists. In fluorous synthetic techniques, reaction components are typically attached to fluorous groups such as perfluoroalkyl groups to facilitate the separation of products. In general, fluorous-tagged molecules partition preferentially into a fluorous phase while non-tagged ones partition into an organic phase. Although fluorous synthetic and/or separation techniques are promising, such techniques are currently limited by a lack of availability of suitable fluorous tags.

It is thus very desirable to develop fluorous tagging compounds and methods of increasing the fluorous nature of compounds.

SUMMARY OF THE INVENTION

In one aspect, the present invention provides a method of increasing the fluorous nature of a compound. The method includes the step of reacting the compound with at least one second compound having the formula:

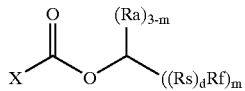

wherein Rf is a fluorous group (for example, a fluoroalkyl group, a fluorinated ether or another highly fluorinated group), Rs is a spacer group, d is 1 or 0 (that is, Rs may be present or absent), m is 1, 2 or 3, Ra is an alkyl group and X is a suitable leaving group. Suitable leaving groups include, but are not limited to, a halide (F, Cl, Br or I), —N$_3$, CN, RO—, NH$_2$O—, NHRO—, NR$_2$O—, RCO$_2$—, ROCO$_2$—, RNCO$_2$—, RS—, RC(S)O—, RCS$_2$—, RSC(O)S—, RSCS$_2$—RSCO$_2$—, ROC(S)O—, ROCS$_2$—, RSO$_2$—, RSO$_3$—, ROSO$_2$—, ROSO$_3$—, RPO$_3$—, ROPO$_3$—, an N-imidazolyl group, an N-triazolyl group, an N-benzotriazolyl group, a benzotriazolyloxy group, an imidazolyloxy group, an N-imidazolinone group, an N-imidazolone group, an N-imidazolinethione group, an N-imidazolinthione group, an N-succinimidyl group, an N-phthalimidyl group, an N-succinimidyloxy group, an N-phthalimidyloxy group, —ON=C(CN)R, or a 2-pyridyloxy group. R is preferably an alkyl group or an aryl group.

The terms "alkyl", "aryl" and other groups refer generally to both unsubstituted and substituted groups unless specified to the contrary. Unless otherwise specified, alkyl groups are hydrocarbon groups and are preferably C$_1$–C$_{15}$ (that is, having 1 to 15 carbon atoms) alkyl groups, and more preferably C$_1$–C$_{10}$ alkyl groups, and can be branched or unbranched, acyclic or cyclic. The above definition of an alkyl group and other definitions apply also when the group is a substituent on another group. The term "aryl" refers to phenyl (Ph) or napthyl, substituted or unsubstituted. The terms "alkylene" refers to bivalent forms of alkyl.

The groups set forth above, can be substituted with a wide variety of substituents. For example, alkyl groups may preferably be substituted with a group or groups including, but not limited to, halide(s). Preferably, halide constituents are F and/or Cl. Aryl groups may preferably be substituted with a group or groups including, but not limited to, halide(s), alkyl group(s), a cyano group(s) and nitro group(s). As used herein, the terms "halide" or "halo" refer to fluoro, chloro, bromo and iodo. Preferred halide substituents are F and Cl.

The resulting fluorous "tagged" compound can be used in a variety of fluorous reaction and/or separation techniques. Such fluorous reaction and separation techniques are disclosed, for example, in U.S. Pat. Nos. 5,859,247 and 5,777,121 and U.S. patent application Ser. No. 09/506,779, assigned to the assignee of the present invention, the disclosures of which are incorporated herein by reference.

Preferably, the molecular weight of the fluorous tag of the present invention does not exceed about 2,500. More preferably, the molecular weight does not exceed about 2,000. Even more preferably the molecular weight does not exceed about 1,750. Compounds may bear more than one fluorous tag of the present invention.

In another aspect, the present invention provides a compound (a fluorous tagging compound) having the formula:

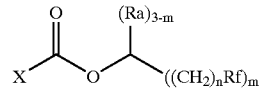

wherein Rf is a fluorous group (for example, a fluoroalkyl group, a fluorinated ether or another highly fluorinated group), n is an integer between 0 and 6, m is 1, 2 or 3, Ra is an alkyl group and X is a leaving group. Ra is preferably C$_1$–C$_6$ alkyl group.

As used herein, the term "fluorous", when used in connection with an organic (carbon-containing) molecule, moiety or group, refers generally to an organic molecule, moiety or group having a domain or a portion thereof rich in carbon-fluorine bonds (for example, fluorocarbons or perfluorocarbons, fluorohydrocarbons, fluorinated ethers and fluorinated amines). The term "fluorous compound," thus refers generally to a compound comprising a portion rich in carbon-fluorine bonds. As used herein, the term "perfluorocarbons" refers generally to organic compounds in which all hydrogen atoms bonded to carbon atoms have been replaced by fluorine atoms. The terms "fluorohydrocarbons" and "hydrofluorocarbons" include organic compounds in which at least one hydrogen atom bonded to a carbon atom has been replaced by a fluorine atom. A few examples of suitable fluorous groups Rf for use in the present invention include, but are not limited to, —C$_4$F$_9$, —C$_6$F$_{13}$, —C$_8$F$_{17}$, —C$_{10}$F$_{21}$, —C(CF$_3$)$_2$C$_3$F$_7$, —C$_4$F$_8$CF(CF$_3$)$_2$, and —CF$_2$CF$_2$OCF$_2$CF$_2$OCF$_3$.

As used herein, the term "tagging" refers generally to attaching a fluorous moiety or group (referred to as a "fluorous tagging moiety" or "tagging group") to a compound to create a "fluorous tagged compound". Separation of the tagged compounds of the present invention is achieved by using fluorous separation techniques that are based upon differences between/among the fluorous nature of a mixture of compounds. As used herein, the term "fluorous separation technique" refers generally to a method that is used to separate mixtures containing fluorous molecules or organic molecules bearing fluorous domains or tags from each other and/or from non-fluorous compounds based predominantly on differences in the fluorous nature of molecules (for example, size and/or structure of a fluorous molecule or domain or the absence thereof). Fluorous separation techniques include but are not limited chromatography over solid fluorous phases such as fluorocarbon bonded phases or fluorinated polymers. See, for example, Danielson, N. D. et al., "Fluoropolymers and Fluorocarbon Bonded Phases as Column Packings for Liquid Chromatography," *J. Chromat.*, 544, 187–199 (1991). Examples of suitable fluorocarbon bonded phases include commercial Fluofix® and Fluophase™ columns available from Keystone Scientific, Inc. (Bellefonte, Pa.), and FluoroSep™-RP-Octyl from ES Industries (Berlin, N.J.). Other fluorous separation techniques include liquid-liquid based separation methods such as liquid-liquid extraction or countercurrent distribution with a fluorous solvent and an organic solvent.

BRIEF DESCRIPTION OF THE DRAWINGS

FIG. 9 illustrates the isolated yields of the 96-compound library of FIG. 8.

DETAILED DESCRIPTION OF THE INVENTION

Carbamates are an important class of protecting group for nitrogen. For example, virtually all peptide synthesis schemes rely on carbamate protecting groups of some sort, and carbamates are commonly used in alkaloid synthesis and other areas. One of the most useful carbamates is the tert-butyloxycarbonyl group (commonly referred to as the "BOC" group) illustrated below:

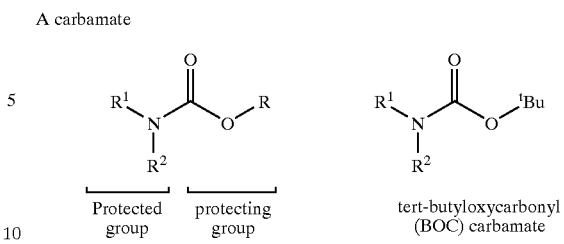

A carbamate

Protected group / protecting group tert-butyloxycarbonyl (BOC) carbamate

In the present invention, a new class of fluorous carbamates referred to herein as fluorous BOC compounds or groups were synthesized after the BOC group. The fluorous tagging groups of the present invention can, for example, be reacted with nitrogen-bearing groups such as amine groups ($-NR^1R^2$) of compounds to create a fluorous-tagged (or protected) compound.

The fluorous BOC ($^F$BOC) groups of the present invention generally act like traditional BOC and other carbamate groups to protect nitrogen-based functional groups during organic reactions. Protecting groups are discussed generally in Greene, T. W.; Wuts, P. G. M. *Protective Groups in Organic Synthesis*; 3rd ed.; Wiley-Interscience: New York, (1999) and Kocienski, P. "Protecting groups", *Thieme*: Stuttgart (1994). However, the fluorous BOC groups of the present invention have advantages over other traditional carbamate and other protecting groups in that they facilitate separation of the $^F$BOC-protected (fluorous-tagged) products from each other and from non-tagged reaction components. Additionally, the fluorous domain of the fluorous BOC groups are useful not only for attachment to nitrogen, but also to oxygen, sulfur and other heteroatoms. The resulting $^F$BOC carbonates, thiocarbamates, etc. serve substantially the same purpose and are used analogously to the $^F$BOC carbamates described in greater detail herein.

Figure 1:
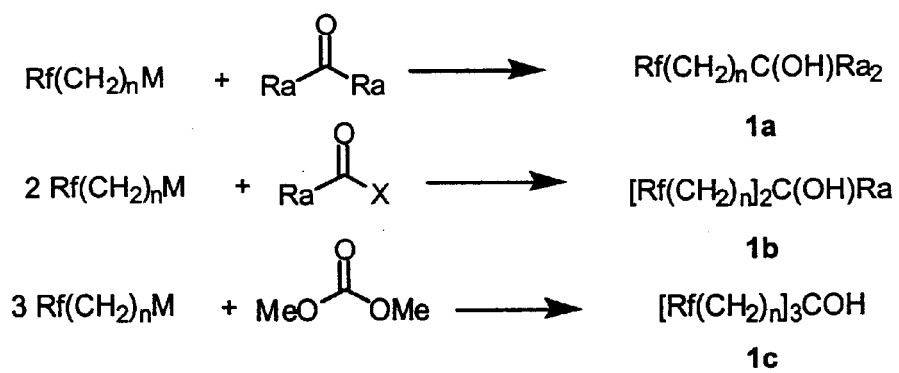
FIG. 1 illustrates synthesis and introduction of fluorous BOC groups.
Figure 1:
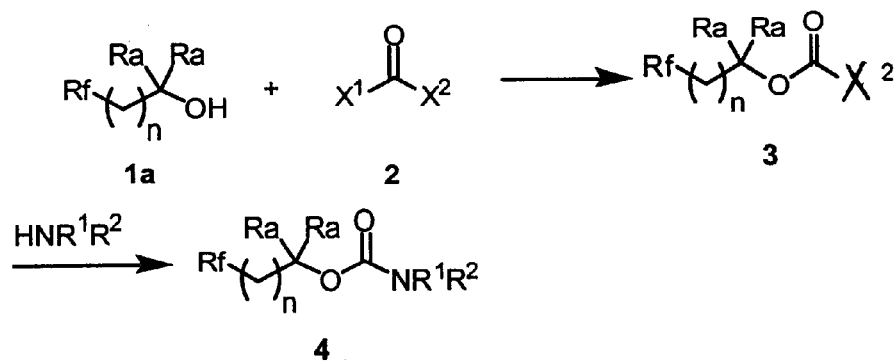

The reagents used for the protection of amines with fluorous BOC groups are generally prepared as shown in FIG. 1. Fluorous alcohols 1a–c bearing one, two or three fluorous chains are readily synthesized, for example, by nucleophilic addition reactions. Addition of an organometallic reagent Rf(CH$_2$) M (wherein, M is, for example, lithium, magnesium halide, etc. and Rf is a fluorous group) to an appropriate ketone generates an alcohol 1a with one fluorous chain and two alkyl groups. Similarly, alcohols with two fluorous chains 1b can be generated by organometallic addition to esters, acids chlorides or related molecules, and alcohols with three fluorous chains 1c can be generated by nucleophilic additions to carbonate esters, phosgene, or related molecules. The alcohols with two and three fluorous chains prepared by these routes usually contain the same fluorous group, but alcohols with different fluorous groups can be prepared by several routes. For example, addition of Rf$^1$(CH$_2$)$_{n1}$M to an aldehyde followed by oxidation of the resulting secondary alcohol and addition of Rf$^2$(CH$_2$)$_{n2}$M results in an alcohol with two different fluorous chains (Rf$^1$ and Rf$^2$) spaced by alkylene spacers that can be the same or different. A series of fluorous alcohols with different numbers of fluorines is useful, for example, in fluorous mixture synthesis techniques. See, U.S patent application Ser. No. 09/506,779.

Fluorous BOC reagents 3 can be prepared by one of many schemes known to those skilled in the art for the conversion of standard alcohols to activated carbamoylating agents. For example, alcohols bearing one fluorous chain and two alkyl groups can react with one of many reagents 2, which can be considered as doubly activated derivatives of carbonic acids. In FIG. 1, the leaving group (X) is a part of the molecule that is cleaved in the substitution reaction. Many different leaving groups suitable for use in the present invention are known to those skilled in the art. For the purposes of this invention, leaving groups whose conjugate acids have a pKa of less than about 18 are preferred. Leaving groups whose conjugate acids have a pKa of less than about 10 are more preferred. Even more preferred are leaving groups whose conjugate acids have a pKa of less than about 5. In a preferred method, the fluorous alcohol 1a is first reacted with the reagent 2 to displace the first leaving group to give 3. The intermediate BOC reagent 3 may be isolated prior to reaction with an amine under standard conditions, or it may be reacted directly with the amine in situ without isolation. Either or both of the acylation reactions may be catalyzed by standard catalysts known to those skilled in the art. An example on one such acylation catalyst is 4-dimethylaminopyridine (DMAP). Fluorous BOC reagents with two or three fluorous chains are prepared and reacted analogously to those with one chain.

Reactions and Compounds in the Examples

Figure 2:
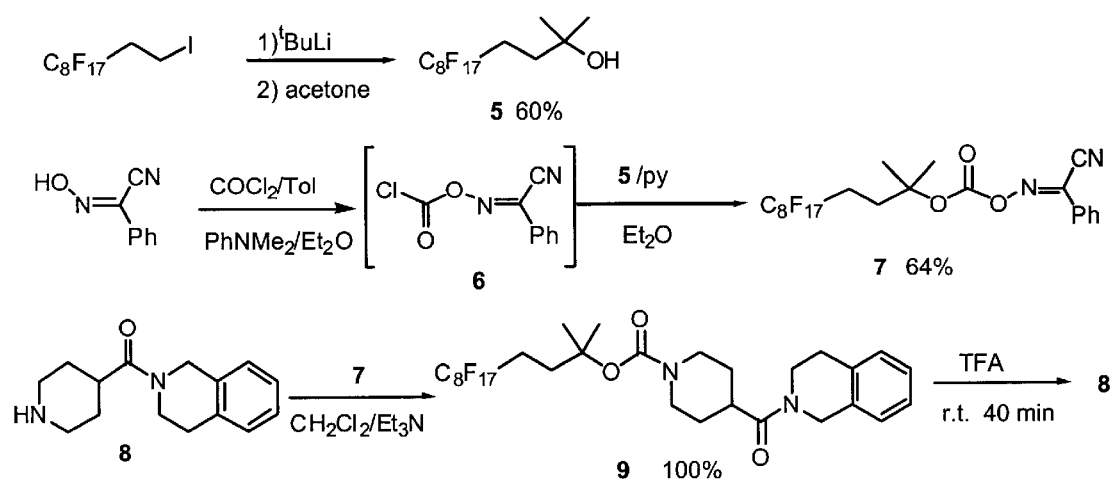
FIG. 2 illustrates synthesis of a fluorous BOC reagent of the present invention and its attachment to an amine and detachment from the resulting amide.

The synthesis of a representative fluorous BOC ($^F$BOC) reagent 7 of the present invention and its attachment to a typical amine 8 and detachment from the resulting amide 9 are shown in FIG. 2. Reaction of perfluorooctylethyl iodide with t-BuLi followed by addition of acetone and workup and chromatographic purification provided the alcohol 5 in 60% yield. Activated reagent 6 was generated according to the literature methods set forth in M. Itoh, et. al, *Bull. Chem. Soc. Jpn.*, 50, 718 (1977), and then reacted with alcohol 5. Workup and chromatography provided the representative $^F$BOC reagent 7 as a solid. Protection of amino amide 8 with the $^F$BOC reagent 7 was accomplished under standard conditions and gave $^F$BOC derivative 9 in quantitative yield. $^F$BOC-protected 9 could be deprotected to regenerate 8 by treatment with neat TFA for 40 min followed by evaporation and vacuum drying to remove the fluorous BOC remnants and other volatile compounds. The fluorous BOC remnants can also be removed by solid phase extraction over fluorous reverse phase silica gel.

Figure 3:
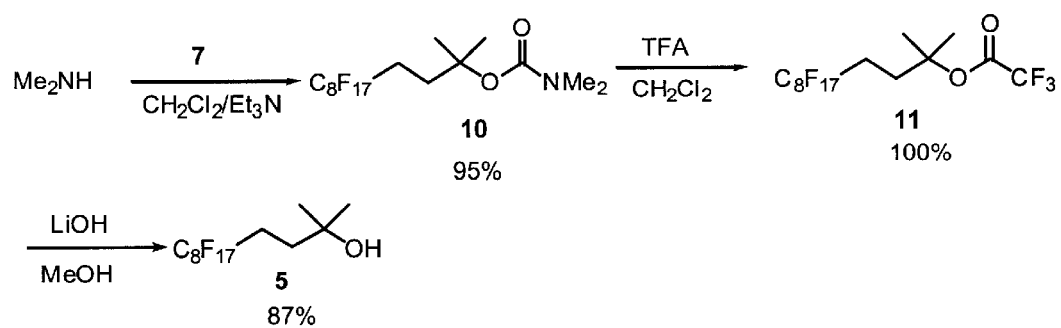
FIG. 3 illustrates recovery of a fluorous BOC compound of the present invention.

The ability to recover the fluorous BOC component for reuse is demonstrated by the results of FIG. 3. Coupling of 7 with dimethyl amine provided 10 in 95% yield. Cleavage of 10 with 30/70 CH$_2$Cl$_2$/TFA followed by evaporation provided the trifluoroacetate 11 in 100% yield. Trifluoroacetate 11 was hydrolyzed by treatment with lithium hydroxide in methanol to provide the starting alcohol 5 in 87% yield.

Figure 4:
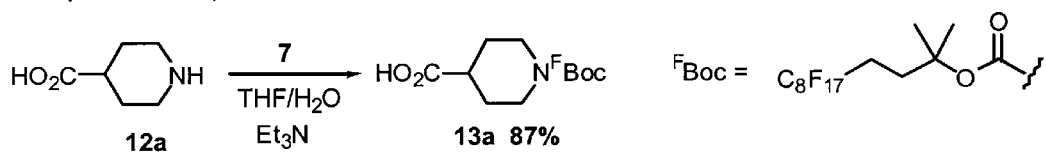
FIG. 4 illustrates the utility of fluorous BOC compounds of the present invention in separating a library of compounds.
Figure 4:
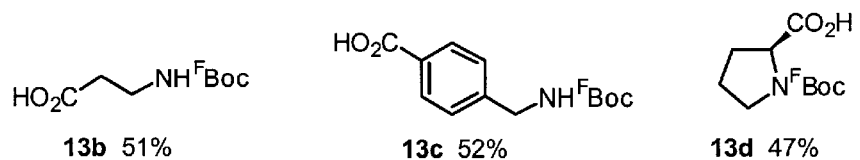
Figure 4:
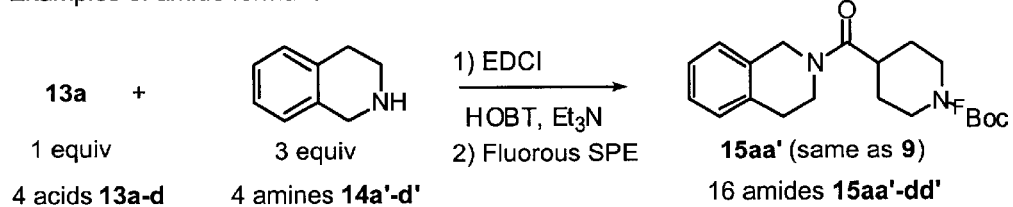
Figure 4:
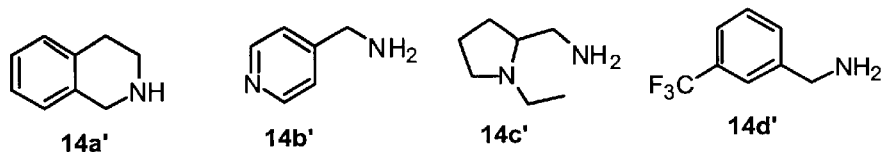
Figure 5:
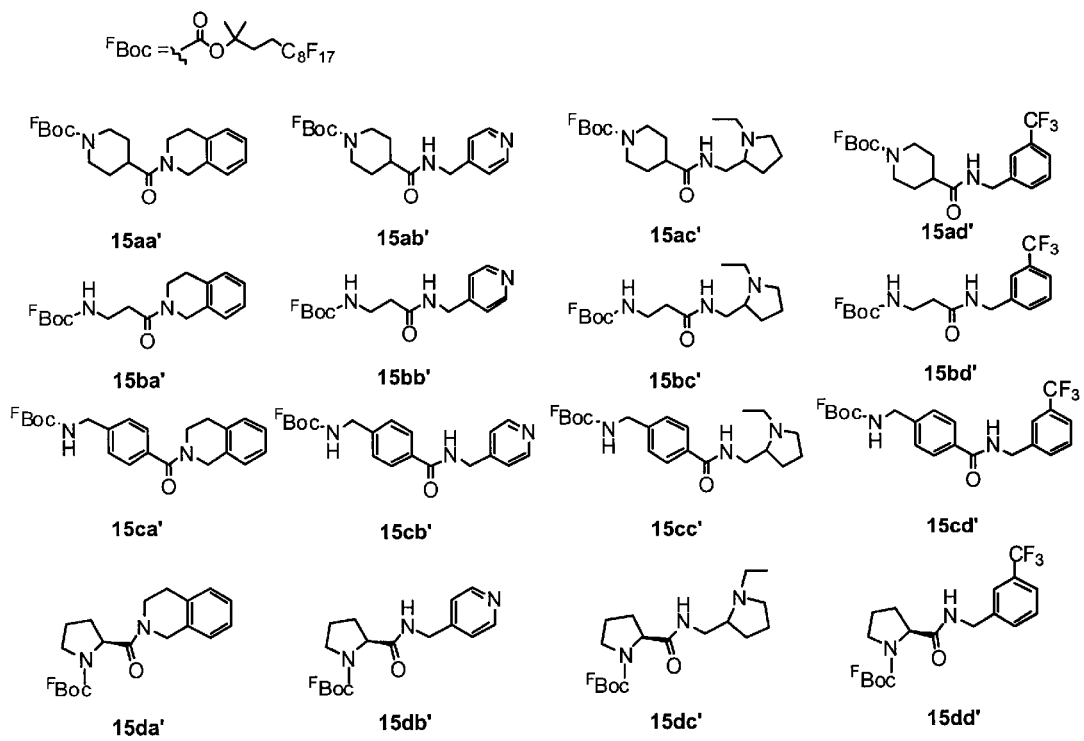
FIG. 5 illustrates the structure of several amides generated from fluorous BOC tagging compounds of the present invention.

To demonstrate the utility of the fluorous BOC group in facilitating reaction separation, a 16 compound library of amides was made by parallel synthesis as shown in FIG. 4. Amines 12a–d were reacted with the $^F$BOC reagent 7 as in FIG. 2 to give $^F$BOC protected acids 13a–d. Each of the four acids was coupled with amines 14a'–d' under standard amide formation conditions using 1-(3-dimethylaminopropyl)-3-ethylcarbodiimide hydrochloride (EDI), N-hydroxybenzotriazole (HOBt), and triethylamine (Et$_3$N). These reaction mixtures were purified by solid phase extraction using a commercially available semi-preparative Fluofix column. The fluorous tagged products are readily separated from all non-tagged reaction components. Yields and structures for the coupled products 15aa'–dd' are illustrated in FIG. 5.

Figure 6:
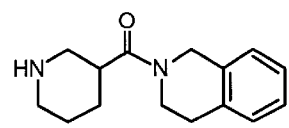
FIG. 6 illustrates several products generated by deprotection of fluorous BOC protected amines.
Figure 6:
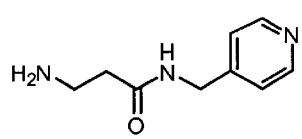
Figure 6:
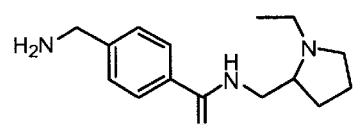
Figure 6:
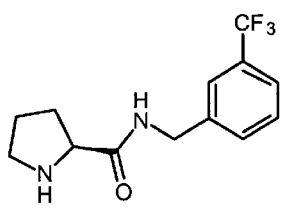

To demonstrate the removal of the fluorous BOC group, four of the products were heated in 3N HCl/MeOH at 60° C. for 16 h. All the volatile products (including the residual fluorous products) were removed by exposure to high vacuum, and then the yields of the final amine hydrochlorides were determined by NMR analysis as described in the Examples. These products are shown in FIG. 6. A second library of eight amines involving the steps of $^F$BOC protection, amide formation with rapid purification by fluorous solid phase extraction, and removal of the $^F$BOC group with TFA, is also described in Example 15. The resulting secondary amines were used to make 96 tertiary amines.

Figure 7:
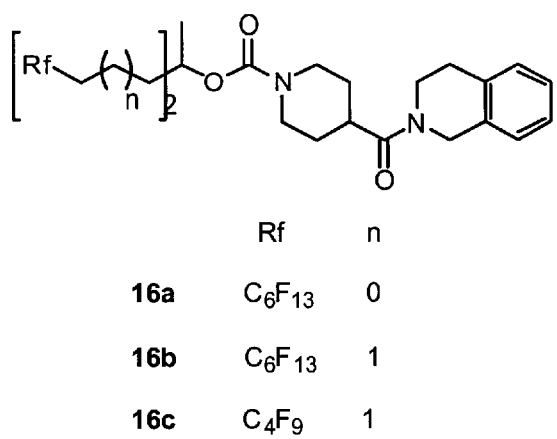
FIG. 7 illustrates fluorous BOC groups with different fluorine content and spacer groups.

The amides shown in FIG. 7 were prepared to demonstrate that other fluorous BOC groups with different numbers of fluorous chains and different spacer elements could also be used. The syntheses of the respective $^F$BOC precursors and the amides themselves are described in the Examples. The retention times of amides 16a–c were then measured on an analytical Fluofix column, eluting with the gradient shown in FIG. 7. The retention times of these amides are all longer than that of amide 9. This is expected because they have more fluorines. Under these conditions, most non-fluorous tagged organic compounds have retention times at or near the solvent front (approximately 2–3 minutes). Since 9 can be separated by fluorous solid phase extraction, it follows that the more strongly retained amides 16a–c will also be separable from non-tagged compounds by solid phase extraction.

EXPERIMENTAL EXAMPLES

Example 1

Authentic Sample of (3,4-Dihydro-1H-isoquinolin-2-yl)piperidin-4-yl-methanone (8).

N-Trifluoroacetyl isonipecotic acid (2.56 g, 11.4 mmol), tetrahydroisoquinoline (1.82 g, 13.7 mmol), EDCI (2.63 g, 13.7 mmol), HOBT (1.85 g, 13.7 mmol) and triethylamine (1.38 g, 13.7 mmol) were stirred in dry dichloromethane (30 mL) at 25° C. for 6 h. The reaction was quenched with water and the aqueous phase was extracted with dichloromethane. The combined organic phase was dried over MgSO$_4$ and purified by column chromatography (40/60 EtOAc/hexanes). The solid obtained was stirred with excess K$_2$CO$_3$ in MeOH at 25° C. overnight (16 h). After evaporation of MeOH, the residue was partitioned between dichloromethane and basic water. Evaporation of the organic phase gave pure product as a colorless solid (2.12 g, 76% for two steps). $^1$H NMR (CDCl$_3$) (mixture of two rotamers) δ 7.23–7.16 (m, 4H), 4.73 (s, 1H), 4.67 (s, 1H), 3.83 (t, J=5.9 Hz, 1H), 3.74 (t, J=5.8 Hz, 1H), 3.21–3.16 (m, 2H), 2.92 (t, J=5.7 Hz, 1H), 2.85 (t, J=5.7 Hz, 1H), 2.76–2.67 (m, 3H), 2.29 (s, 1H), 1.80–1.73 (m, 4H); $^{13}$C NMR (CD$_3$OD-CDCl$_3$) δ 6 175.5, 175.3, 135.8, 135.1, 134.0, 133.8, 129.6, 129.3, 127.9, 127.6, 127.4, 127.3, 127.0, 48.2, 45.8, 45.4, 44.2, 41.4, 40.2, 39.6, 39.5, 30.5, 29.5, 29.4, 29.1; LRMS: m/z (relative intensity), 244 (M$^+$, 37%), 188 (100%), 132 (74%); HRMS: calcd. for C$_{15}$H$_{19}$N$_2$O 244.1576, found 244.1574. MP: 75–76° C.

Example 2

1,5-Bis(perfluorohexyl)-3-methylpentan-3-ol

A portion of 2-perfluorohexylethyl iodide (1.0 mL) was added to a suspension of Mg powder (0.85 g, 35.0 mmol) in dry diethyl ether (5 mL) under argon. The mixture was sonicated for 30 min. To the resulting suspension, a solution of 2-perfluorohexylethyl iodide (total 7.8 ml, 31.8 mmol) in dry diethyl ether (40 mL) was added over 40–60 min. Upon completion of addition, the dark mixture was stirred at reflux for 1 h. After cooling down to room temperature, a solution of ethyl acetate (0.9 mL, 11.1 mmol) in diethyl ether (4.0 mL) was added slowly. The mixture was stirred at room temperature overnight before quenching with saturated aqueous NH$_4$Cl. The aqueous phase was extracted with diethyl ether (3×20 mL). The ether phase was combined and dried over MgSO$_4$. After evaporation of solvent, the residue was purified by column chromatography with 5:95 ethyl acetate-hexane. The title compound obtained was further recrystallized twice from chloroform to give colorless needles (5.18 g, 79%). $^1$H NMR (CDCl$_3$) δ 2.34–2.10 (m, 4H), 1.89–1.68 (m, 4H), 1.28 (s, 3H), 1.17 (s, 1H); $^{13}$C NMR (CDCl$_3$) δ 70.5, 32.0, 26.2, 25.7 (t); IR (Nujol) 3467, 2923, 1461, 1369, 1244, 1140, 1051, 701, 521 cm$^{-1}$; LRMS m/z: 1491 (50%), 1145 (5%), 723 (42%), 375 (100%); HRMS found: C, 29.04%, H, 1.62%. Calcd.: C, 29.28%, 1.64%. MP: 57–58° C.

Example 3

O-Bis(perfluorohexylethyl) ethyloxycarbonyloxyiminophenylaceto nitrile

To a sample tube sealed under argon was charged with a solution of phosgene in toluene (0.27 mL, 0.55 mmol) and the solution was cooled to 0° C. A solution of 2-hydroxyimino-2-phenylacetonitrile (75 mg, 0.51 mmol) and dimethylaniline (70 uL, 0.55 mmol) in THF (0.2 mL) and benzene (0.2 mL) was added dropwise to the ice-cooled solution. The mixture was stirred at 0° C. for 6 h. The mixture was placed in a freezer (−20° C.) overnight before returning to the ice bath. A solution of the alcohol from Example 2 (0.39 g, 0.55 mmol) and pyridine (45 uL, 0.55 mmol) in THF (3.0 mL) was added dropwise. The orange mixture was stirred at 0° C. for 6 h and allowed to warm to room temperature over night. The suspension was quenched with water and extracted with diethyl ether. The organic phase was dried over MgSO$_4$. After removal of solvent, the residue was purified by column chromatography with 5:95 ethyl acetate-hexanes to give pure product as a white gum (223 mg, 49%). $^1$H NMR (CDCl$_3$) δ 7.95 (d, J=7.5 Hz, 2H), 7.61 (t, J=7.3 Hz, 1H), 7.51 (t, J=7.7 Hz, 2H), 2.42–2.08 (m, 8H), 1.66 (s, 3H); $^{13}$C NMR (CDCl$_3$) δ 149.7, 138.7, 133.3, 129.4, 127.6, 108.2, 86.1, 28.8, 25.6 (t), 22.8; IR (thin film): 1795, 1450, 1240, 1023, 940, 729 cm$^{-1}$; FABMS m/z: 910 (M$^+$, absent), 867 (M$^+$−CO$_2$, 21%), 721 (100%), 681 (16%).

Example 4

1,7-Bis(perfluorobutyl)-4-methylheptan-4-ol

To a solution of 3-perfluorobutylpropyl iodide (688 mg, 1.77 mmol) in a mixture of dry diethyl ether and dry hexane (25 mL, 1:1 v/v) was added $^t$BuLi (2.2 mL, 1.7 M in pentane, 3.74 mmol) at −78° C. The mixture was stirred for 1 h during which time the temperature increased to −35° C. After cooling to −78° C., acetyl chloride (57 uL, 0.80 mmol) was added dropwise. The cooling bath was removed and the reaction mixture was stirred for 1 h. Water was added to quench the reaction. After extraction with ether, the organic phase was dried over MgSO$_4$ and evaporated to dryness. The crude product was purified by column chromatography with 5:95 ethyl acetate-hexane to give the alcohol as a yellow oil (103 mg, 23%). $^1$H NMR (CDCl$_3$) δ 2.19–2.01 (m, 4H), 1.76–1.68 (m, 4H), 1.67–1.53 (m, 4H), 1.24 (s, 3H); $^{13}$C NMR (CDCl$_3$) δ 121.8–110.8 (m), 72.4, 41.4, 31.3, 26.7, 15.1; LRMS m/z (relative intensity) 551 (M$^+$−Me, 15%), 305 (100%); HRMS found: 551.0676, calcd. for C$_{15}$H$_{13}$F$_{18}$O: 551.0679; IR (thin film): 3147, 2975, 1468, 1356, 1206, 880, 720 cm$^{-1}$.

Example 5

1,7-Bis(perfluorohexyl)-4-methylheptan-4-ol

This compound was prepared by the same procedure as Example 4 but ethyl acetate was used instead of acetyl chloride. Yield: 68% (white solid). $^1$H NMR (CDCl$_3$) δ 2.13–2.04 (m, 4H), 1.76–1.66 (m, 4H), 1.64–1.53 (m, 4H), 1.24 (s, 3H); $^{13}$C NMR (CDCl$_3$) δ 122.0–107.0 (m), 72.4, 41.4, 31.4 (t), 26.5, 15.1; $^{19}$F NMR (CDCl$_3$) δ −81.2 (3F), −114.8 (2F), −122.4 (2F), −123.4 (2F), −124.1 (2F), −126.6 (2F); LRMS: m/z (relative intensity) 751 (M$^+$−Me, 77%), 709 (24%), 405 (100%); HRMS found: 751.0570, calcd. for C$_{19}$H$_{13}$OF$_{26}$: 751.0566; MP: 46–47° C.

Example 6

4-Perfluorooctyl-2-methylbutan-2-ol (5)

This compound was prepared by the same procedure as Example 4 but acetone was used instead of acetyl chloride. Yield: 60% (white solid). $^1$H NMR (CDCl$_3$) δ 2.32–2.14 (m, 2H), 1.78–1.73 (m, 2H), 1.29 (s, 6H); $^{13}$C NMR (CDCl$_3$) δ 122.4–107.4 (m), 69.9, 33.5, 29.4, 26.2 (t); LRMS m/z (relative intensity) 505 (M$^+$−H, 1296), 491 (M$^+$−Me, 100%); HRMS found: 491.0306; calcd. for C$_{12}$H$_8$F$_{17}$O: 491.0304. MP: 50–51° C.

Example 7

O-Bis(perfluorobutylpropyl) ethoxycarbonyloxyiminophenylaceton trile

This compound was prepared by the same procedure as Example 3. Yield: 27% (gum). $^1$H NMR (CDCl$_3$) δ 7.95 (d, J=8.1 Hz, 2H), 7.60 (t, J=7.2 Hz, 1H), 7.51 (t, J=7.5 Hz, 2H), 2.20–1.91 (m, 8H), 1.79–1.71 (m, 4H), 1.62 (s, 3H); $^{13}$C NMR (CDCl$_3$) δ 150.0, 138.3, 133.2, 129.4, 127.6, 121.5–114.8 (m), 108.4, 88.7, 37.5, 30.8 (t), 23.1, 14.8; LRMS m/z (relative intensity) 761 (M$^+$+Na), 548 (45%), 305 (100%), 287 (90%). IR (thin film): 2982, 1795, 1234, 1132, 1022, 878 cm$^{-1}$.

Example 8a

O-(Perfluorooctylethyl) isopropanoxycarbonyloxyiminophenylacet onitrile (7)

This compound was prepared by the same procedure as Example 3. Yield: 61% (orange solid). $^1$H NMR (CDCl$_3$) δ 7.95 (d, J=8.1 Hz, 2H), 7.60 (t, J=6.9 Hz, 1H), 7.51 (t, J=7.8 Hz, 2H), 2.29–2.15 (m, 4H), 1.66 (s, 6H); $^{13}$C NMR (CDCl$_3$) δ 150.0, 138.3, 133.3, 129.5, 127.9, 127.7, 111.0, 85.9, 31.5, 25.7; $^{19}$F NMR (CDCl$_3$) δ −79.6 (3F), −113.2 (2F), −120.7 (6F), −121.5 (2F), −121.9 (2F), −124.9 (2F); LRMS: 634 (16%), 615 (10%), 489 (100%); MP: 76–78° C.

Example 8b 4-(3,4-Dihydro-1H-isoquinoline-2-carbonyl)-piperidine-1-carboxylic acid 4,4,5,5,6,6,7,7,8,8,9,9,10,10,11,11,11-heptadecafluoro-1,1,-dimethyl-undecyl ester A solution of compound 7 (89 mg, 0.13 mmol) and compound 8 (29 mg, 0.12 mmol) in dichloromethane (4 ml) was stirred at room temperature for 2 h. The mixture was evaporated to dryness. The residue was purified by column chromatography (3:1 EtOAc/hexanes) to give compound 9 (93 mg, 100%) as a white solid. $^1$H NMR (CDCl$_3$) δ 7.22–7.14 (m, 4H), 4.74 (s, 1H), 4.68 (s, 1H), 4.23–4.07 (br, 2H), 3.8 (br, 1H), 3.74 (t, J=2.9 Hz, 1H), 2.96–2.74 (m, 5H), 2.22–2.01 (m, 4H), 1.74 (br, 4H), 1.51 (s, 6H); $^{13}$C NMR (CDCl$_3$) δ 173.4, 173.2, 154.2, 135.3, 133.9, 133.6, 132.6, 129.3, 128.5, 127.3, 126.9, 126.8, 126.6, 126.1, 47.5, 44.7, 43.8, 43.3, 40.2, 39.1, 38.9, 32.1, 30.0, 28.5, 26.2; LRMS: 776 (M$^+$, 15%) 757 (27%), 739 (22%), 243 (100%), 188 (60%), 132 (45%); HRMS: calcd. for C$_{29}$H$_{29}$N$_2$O$_3$F$_{17}$: 776.1907, found 776.1894. MP: 114–116° C.

Example 9

4-(3,4-Dihydro-1H-isoquinoline-2-carbonyl) piperidine-1-carboxylic acid 1-perfluorooctylethylisopropyl ester (16a)

The fluorous Boc reagent from Example 3 (89 mg, 0.13 mmol), the compound in Example 1 (29 mg, 0.12 mmol) and triethylamine (20 mg, 20.0 mmol) were mixed in dry dichloromethane (4.0 mL) and stirred at room temperature for 2 h. After evaporation of solvent, the residue was purified by column chromatography with 30:70 ethyl acetate-hexane to give pure product as a white solid. Yield: 93 mg (96%); Rf=0.22 (30:70 ethyl acetate-hexane); $^1$H NMR (mixture of two rotamers) (CDCl$_3$) δ 7.22–7.14 (m, 4H), 4.74 (s, 1H), 4.68 (s, 1H), 4.23–4.07 (br, 2H), 3.85 (br, 1H), 3.74 (t, J=5.8 Hz, 1H), 2.95–2.74 (m, 5H), 2.22–2.05 (m, 4H), 1.74 (br, 4H), 1.52 (s, 6H); $^{13}$C NMR (CDCl$_3$) δ 173.4, 173.2, 154.2, 135.3, 134.0, 133.6, 132.6, 129.3, 128.5, 127.3, 126.9, 126.8, 126.6, 126.1, 122.8–107.3 (m), 79.9, 47.5, 44.7, 43.8, 43.3, 40.2, 39.1, 38.9, 32.1, 30.0, 28.5, 26.2; LRMS: m/z (relative intensity) 776 (M$^+$, 14%), 757 (M$^+$-F, 25%) 739 (M$^+$-2F, 20%), 489 (11%), 287 (20%), 271(24%), 243 (100%), 188 (60%), 132 (45%); HRMS calcd. for C$_{29}$H$_{29}$N$_2$O$_3$F$_{17}$: 776.1907, found: 776.1894; MP: 115° C.

Example 10

Compound 16b

This compound was prepared by the same procedure as Example 9 with the fluorous Boc reagent from Example 8. Yield: 79% (yellowish oil); $^1$H NMR (CDCl$_3$) δ 7.22–7.14 (m, 4H), 4.74 (s, 1H), 4.68 (s, 1H), 4.16 (br, 2H), 3.85 (br, 1H), 3.74 (t, J=5.8 Hz, 1H), 2.95–2.74 (m, 5H), 2.18–2.00 (m, 6H), 1.75–1.60 (m, 10 H), 1.46 (s, 3H); $^{13}$C NMR (CDCl$_3$) δ 173.4, 173.2, 154.2, 135.3, 134.0, 133.7, 132.7, 129.5, 129.0, 128.7, 128.2, 127.5, 127.0, 126.7, 126.3, 125.0, 123.3–108.7 (m), 82.7, 47.6, 44.7, 43.3, 40.2, 39.0, 38.7, 38.3, 37.9, 31.4, 30.8, 30.3, 30.0, 28.5 (t), 24.6, 23.7, 14.9 (t); LRMS: m/z (relative intensity) 835 (M$^+$-H, 35%), 817 (M$^+$-F, 23%), 548 (17%), 287 (77%), 243 (100%), 188 (72%), 132 (71%).

Example 11

Compound 16c

This compound was prepared by the same procedure as Example 9 with the fluorous Boc reagent from Example 7. Yield: 100% (white solid); $^1$H NMR (CDCl$_3$) δ 7.22–7.14 (m, 4H), 4.74 (s, 1H), 4.68 (s, 1H), 4.23–4.07 (br, 2H), 3.8 (br, 1H), 3.74 (t, J=2.9 Hz, 1H), 2.96–2.74 (m, 5H), 2.22–2.01 (m, 4H), 1.74 (br, 4H), 1.51 (s, 6H); $^{13}$C NMR (CDCl$_3$) δ 173.4, 173.2, 154.2, 135.3, 133.9, 133.6, 132.6, 129.3, 128.5, 127.3, 126.9, 126.8, 126.6, 126.1, 47.5, 44.7, 43.8, 43.3, 40.2, 39.1, 38.9, 32.1, 30.0, 28.5, 26.2; LRMS: 776 (M$^+$, 15%) 757 (27%), 739 (22%), 243 (100%), 188 (60%), 132 (45%); HRMS: calcd. for C$_{29}$H$_{29}$N$_2$O$_3$F$_{17}$: 776.1907, found 776.1894. MP: 114–116° C.

Example 12

Dimethyl-carbamic acid 4,4,5,5,6,6,7,7,8,8,9,9,10,10,11,11,11-heptadecafluoro-1,1-dimethylundecyl ester (10)

Dimethylamine (300 uL, 2.0 M in THF, 0.60 mmol) was added to a solution of fluorous Boc reagent 7 (101 mg, 0.15 mmol) in THF. The mixture was stirred at room temperature for 1.5 h. After evaporation of solvent, the residue was purified by column chromatography with 10:90 ethyl acetate/hexane (Rf=0.18) to give pure product (82 mg, 95%); $^1$H NMR (CDCl$_3$) δ 2.87 (s, 6H), 2.24–1.99 (m, 4H), 1.51 (s, 6H); $^{13}$C NMR (CDCl$_3$) δ 155.5, 122.0–105.2 (m), 79.4, 35.9, 32.1, 26.0; LRMS: 577 (M$^+$, 9%), 558 (M$^+$-F, 12%), 489 (45%), 90 (70%), 72 (100%); IR (thin film): 2942, 1707, 1454, 1389, 1236, 656 cm$^{-1}$.

Example 13

Trifluoro-acetic acid 4,4,5,5,6,6,7,7,8,8,9,9,10,10,11,11,11-heptadecafluoro-1,1-dimethylundecyl ester (11)

Dimethylamine (2-perfluorooctylethyl)isopropyl carbamate 10 (251 mg, 0.44 mmol) was stirred with 1:1 CH$_2$Cl$_2$/TFA at room temperature overnight. After evaporation of solvent, the residue was partitioned between dichloromethane and aqueous K$_2$CO$_3$. The organic phase was dried over MgSO$_4$ and evaporated to give pure product (262 mg, 100%); $^1$H NMR (CDCl$_3$)δ 2.22–2.08 (m, 4H), 1.63 (s, 6H); $^{19}$F NMR (CDCl$_3$) δ −74.6 (3F), −79.6 (2F), −113.3 (2F), −120.8 (6F), −121.6 (2F), −122.1 (2F), −125.0 (2F). $^{13}$C NMR (CDCl$_3$) δ 156.4 (t), 121.5–105.1 (m), 86.7, 31.5, 25.7 (t), 25.0; LRMS: m/z (relative intensity) 587 (M$^+$-Me, 70%), 489 (M$^+$-CF$_3$CO$_2$, 68%), 155 (82%); HRMS calcd. for C$_{13}$H$_{10}$F$_{17}$: 489.0511, found: 489.0504,; IR (thin film): 2992, 1784, 1371, 1214 cm$^{-1}$.

Example 14

Synthesis of the Library in FIGS. 4 and 5

1. Piperidine-1,4-dicarboxylic acid mono-(4,4,5,5,6,6,7,7,8,8,9,9,10,10,11,11,11-heptadecafluoro-1,1-dimethylundecyl) ester (13a)

To a solution of fluorous Boc reagent 7 (6.2 g, 9.1 mmol) and triethylamine (1.01 g, 10.0 mmol) in THF was added a solution of isonipecotic acid (1.29 g, 10.0 mmol) in water. The mixture was stirred at room temperature overnight. After removal of solvent, the solid residue as stirred with chloroform (300 mL) and the white solid was filtered off. The organic solvent was evaporated and the residue was recrystallized from chloroform/hexane to give product (2.3 g). The mother liquid was concentrated and purified by column chromatography. The product (total: 5.24 g, 87%) was obtained as a colorless solid. $^1$H NMR (CDCl$_3$) δ 3.97 (br, 2H), 2.99 (t, J=10.9 Hz, 2H), 2.56–2.48 (m, 1H), 2.18–1.91 (m, 6H), 1.72–1.59 (m, 2H), 1.51 (s, 6H); $^{13}$C NMR (CDCl$_3$) δ 180.1, 154.2, 126.1–106.8 (m), 80.1, 43.5, 42.8, 40.8, 31.8, 27.8, 26.2, 25.8; LRMS m/z (relative intensity) 661 (M$^+$, 13%), 642 (M$^+$-F, 41%); HRMS calcd. for C$_{20}$H$_{20}$NO$_4$F$_{17}$: 661.1148, found: 661.1146,; MP: 140–142° C.

2. 3-(4,4,5,5,6,6,7,7,8,8,9,9,10,10,11,11,11-Heptadecafluoro-1,1-dimethyl-undecyloxycarbonylamino)propionic acid (13b)

This compound was prepared by the same procedure as Example 14.1. Yield: 51%. $^1$H NMR (CDCl$_3$) δ 5.08 (br, 1H), 3.42 (q, J=5.7 Hz, 2H), 2.61 (t, J=5.6 Hz, 2H), 2.17–2.04 (m, 4H), 1.49 (s, 6H); LRMS m/z (relative intensity) 622 (M$^+$+H, 6%), 584 (M$^+$-2F, 32%), 562(74%), 489(51%), 133(47%), 116(100%); HRMS: found 622.0874; calcd. for C$_{17}$H$_{17}$NO$_4$F$_{17}$: 622.0886. MP: 94–95° C.

3. 4-[(4,4,5,5,6,6,7,7,8,8,9,9,10,10,11,11,11-Heptadecafluoro-1,1-dimethyl-undecyloxycarbonylamino)-methyl]benzoic acid (13c)

This compound was prepared by the same procedure as Example 14.1. Yield: 52%. $^1$H NMR (MeOH-d4) δ 7.96 (d, J=8.2 Hz, 2H), 7.36 (d, J=8.2 Hz, 2H), 4.30 (s, 2H), 2.20–2.01 (m, 4H), 1.50 (s, 6H); LRMS m/z (relative intensity) 667(M$^+$-F, 59%), 547(63%), 489(54%), 196 (100%), 151(55%). MP: 137–140° C.; HRMS: found: 66.0929; calcd. for C$_{22}$H$_{17}$NO$_3$F$_{17}$: 666.0937

4. (2S)-Pyrrolidine-1,2-dicarboxylic acid 1-(4,4,5,5,6,6,7,7,8,8,9,9,10,10,11,11,11-Heptadecafluoro-1,1-dimethylundecyl)ester (13d)

This compound was prepared by the same procedure as Example 14.1. Yield: 47%. $^1$H NMR (CDCl$_3$) δ 4.37–4.22 (m, 1H), 3.55–3.35 (m, 2H), 2.26–1.93 (m, 8H), 1.52–1.47 (s, 6H); $^{13}$C NMR (MeOH-d4) δ 176.6, 155.5, 120.4–109.2

(m), 81.6, 60.6, 47.8, 32.8, 32.0, 31.1, 27.0, 26.5, 25.3, 24.6; LRMS m/z (relative intensity) 646 ($M^+$-H, 10%), 628 ($M^+$-F, 16%), 489 (56%), 114 (100%), 70 (70%); HRMS calcd. for $C_{18}H_{17}NO_2F_{17}$: 602.0974, found: 602.0988; MP: 75–76° C.

5. General Procedure for the Synthesis of 15

To sixteen vials were added acids 13a–d (0.06 mmol), amines 14a'–d' (0.24 mmol), EDCI (0.09 mmol), HOBT (0.09 mmol) and $Et_3N$ (0.09 mmol). Chloroform (0.5 mL) and DMF (0.5 mL) was added to each vial. These sixteen reaction mixtures were stirred at room temperature for 16 h. After concentration with a vacuum centrifuge, each reaction mixture was injected onto a preparative Fluofix™ 1EW 125 column. The column was eluted with 9:1 MeOH—$H_2O$ for 25 min and followed by pure MeOH for 20 min. The fractions of products were collected and evaporated with a vacuum centrifuge to give the sixteen compound library 15aa'–15dd', which was analyzed by $^1H$ NMR spectroscopy. The isolated yields of the amides are listed in FIG. 5.

15aa' $^1H$ NMR ($CDCl_3$) δ 7.22–7.17 (m, 4H), 4.74 (s, 1H), 4.68 (s, 1H), 4.14–4.10 (m, 2H), 3.84 (s, 1H), 3.74 (t, J=5.7 Hz, 1H), 2.95–2.74 (m, 4H), 2.24–2.05 (m, 4H), 1.74 (br, 4H), 1.51 (s, 6H).

15ab' $^1H$ NMR ($CDCl_3$) δ 8.54 (d, J=6.0 Hz, 2H), 7.16 (d, J=5.8 Hz, 2H), 5.95 (s, 1H), 4.46 (d, J=6.0 Hz, 2H), 4.11 (br, 2H), 2.80 (t, J=11.8 Hz, 2H), 2.34–2.28 (m, 5H) 1.71 (br, 4H), 1.51 (s, 6H).

15ac' $^1H$ NMR ($CDCl_3$) δ 6.08 (s, 1H), 4.08 (br, 2H), 3.53–3.49 (m, 1H), 3.16–3.11 (m, 2H), 2.81–2.74 (m, 3H), 2.52 (br, 1H), 2.26–2.03 (m, 8H), 1.85–1.53 (m, 7H), 1.51 (s, 6H), 1.10 (t, J=7.2 Hz, 3H).

15ad' $^1H$ NMR ($CDCl_3$) δ 7.56–7.43 (m, 4H), 5.85 (t, J=5.4 Hz, 1H), 4.51 (d, J=6.0 Hz, 2H), 4.10 (br, 2H), 2.79 (br, 2H), 2.36–2.06 (m, 5H), 1.87–1.60 (m, 4H), 1.51 (s, 6H).

15ba' $^1H$ NMR ($CDCl_3$) δ 7.24–7.09 (m, 4H), 5.45 (t, J=5.8 Hz, 1H), 4.74 (s, 1H), 4.59 (s, 1H), 3.83 (t, J=6.0 Hz, 1H), 3.65 (t, J=5.9 Hz, 1H), 3.50–3.45 (m, 2H), 2.92–2.85 (m, 2H), 2.61–2.58 (m, 2H), 2.22–1.98 (m, 4H), 1.56 (s, 6H).

15bb' $^1H$ NMR ($CDCl_3$) δ 8.55 (d, J=5.9 Hz, 2H), 7.17 (d, J=5.8 Hz, 2H), 6.35 (s, 1H), 5.29 (s, 1H), 4.46 (d, J=6.0 Hz, 2H), 3.45 (q, J=6.0 Hz, 2H), 2.51 (t, J=5.8 Hz, 2H), 2.11–1.98 (m, 4H), 1.46 (s, 6H).

15bc' $^1H$ NMR ($CDCl_3$) δ 6.16 (br, 1H), 5.38 (s, 1H), 4.14 (br, 2H), 3.67–3.41 (m, 2H), 3.16–3.12 (m, 2H), 2.79–2.75 (m, 2H), 2.55 (br, 1H), 2.42 (br, 1H), 2.24–2.02 (m, 4H), 1.85–1.68 (m, 5H), 1.48 (s, 6H), 1.08 (m, 3H).

15bd' $^1H$ NMR ($CDCl_3$) δ 7.56–7.42 (m, 4H), 6.11 (s, 1H), 5.23 (s, 1H), 4.50 (d, J=5.9 Hz, 2H), 3.48–3.42 (q, J=6.0 Hz, 2H), 2.48 (t, J=5.9 Hz, 2H), 2.22–1.99 (m, 4H), 1.46 (s, 6H).

15ca' $^1H$ NMR ($CDCl_3$) 7.43 (d, J=7.8 Hz, 2H), 7.33 (d, J=7.6 Hz, 2H), 7.18–7.01 (m, 4H), 5.0 (br, 1H), 4.94 (br, 1H), 4.59 (br, 1H), 4.37 (m, 2H), 3.99 (br, 1H), 3.64 (br, 1H), 2.97–2.87 (br, 2H), 2.20–2.06 (m, 4H), 1.53 (s, 6H).

15cb' $^1H$ NMR ($CD_3OD$) δ 8.47 (s, 2H), 7.85 (d, J=8.2 Hz, 2H), 7.39 (d, J=8.0 Hz, 4H), 4.62 (s, 2H), 4.30 (s, 2H), 2.31–2.09 (m, 4H), 1.46 (s, 6H).

15cc' $^1H$ NMR ($CDCl_3$) δ 7.74 (d, J=8.1 Hz, 2H), 7.33 (d, J=7.9 Hz, 2H), 4.36 (s, 2H), 3.71–3.67 (m, 1H), 3.31–3.25 (m, 2H), 2.82–2.79 (m, 2H), 2.28–1.99 (m, 8H), 1.74–1.63 (m, 2H), 1.51 (s, 6H), 1.11 (t, J=7.2 Hz, 3H).

15cd' $^1H$ NMR ($CDCl_3$) δ 7.77 (d, J=8.2 Hz, 2H), 7.60–7.41 (m, 4H), 7.34 (d, J=7.75 Hz, 2H), 6.48 (s, 1H), 4.98 (s, 1H), 4.71 (d, J=5.8 Hz, 2H), 4.36 (s, 2H), 2.36–1.91 (m, 4H), 1.51 (s, 6H).

15da' $^1H$ NMR ($CDCl_3$) δ 7.26–7.11 (m, 4H), 4.83–4.58 (m, 3H), 4.10 (m, 1H), 3.70–3.56 (m, 3H), 2.91–2.84 (m, 2H), 2.24–1.84 (m, 8H), 1.52 (s, 6H).

15db' $^1H$ NMR ($CDCl_3$), δ 8.53 (d, J=4.3 Hz, 2H), 7.43 (s, 1H), 7.17 (d, J=5.7 Hz, 2H), 4.51–4.34 (m, 3H), 3.43–3.36 (m, 2H), 2.40–1.94 (m, 8H), 1.40 (s, 6H).

15dc' $^1H$ NMR ($CDCl_3$) δ 6.91 (s, 1H), 6.42 (s, 1H), 4.29–4.18 (m, 1H), 3.51–3.40 (m, 3H), 3.13–2.05 (m, 2H), 2.75 (m, 1H), 2.52 (m, 1H), 2.26–1.68 (m, 13H), 1.52 (s, 6H), 1.08 (t, J=7.2 Hz, 3H).

15dd' $^1H$ NMR ($CDCl_3$) δ 7.50–7.36 (m, 4H), 4.49–4.23 (m, 4H), 3.49–3.32 (m, 2H), 2.41–1.82 (m, 7H), 1.51 (s, 6H).

6. General Procedure for the Deprotection of 15

Amide 15 (0.05 mmol) was heated with 3N HCl/MeOH (1.0 mL) at 65° C. for 16 h. The mixture was evaporated and dried under high vacuum (~1 mmHg) for 16 h. The yields of products were determined by $^1H$ NMR spectroscopy with p-dimethoxybenzene as an internal standard and are shown in FIG. 6.

Amine from compound 15aa'. $^1H$ NMR ($CDCl_3$) δ 7.21–7.13 (m, 4H), 4.73 (s, 1H), 4.67 (s, 1H), 3.84 (t, J=5.9 Hz, 1H), 3.75–3.69 (m, 1H), 3.24 (br, 2H), 2.95–2.78 (m, 5H), 1.79 (br, 4H).

Amine from compound 15bb'. $^1H$ NMR ($CD_3OD$) δ 8.98 (d, J=5.9 Hz, 2H), 8.21 (d, J=6.0 Hz, 2H), 4.56 (s, 2H), 3.21 (m, 2H), 2.77–2.73 (m, 2H).

Amine from compound 15cc'. $^1H$ NMR ($CD_3OD$) δ 8.01 (d, J=8.1 Hz, 2H), 7.60 (d, J=8.1 Hz, 2H), 4.20 (s, 2H), 3.92–3.58 (m, 5H), 3.30–3.15 (m, 2H), 2.29–2.02 (m, 4H), 1.41 (t, J=6.9 Hz, 3H).

Amine from compound 15dd'. $^1H$ NMR ($CD_3OD$) δ 9.00 (s, 1H), 7.83–7.54 (m, 4H), 4.52 (m, 2H), 4.34–4.29 (m, 1H), 3.73 (s, 2H), 3.43–3.31 (m, 1H), 2.48–2.42 (m, 1H), 2.11–1.98 (m, 2H).

Example 15

Figure 8:
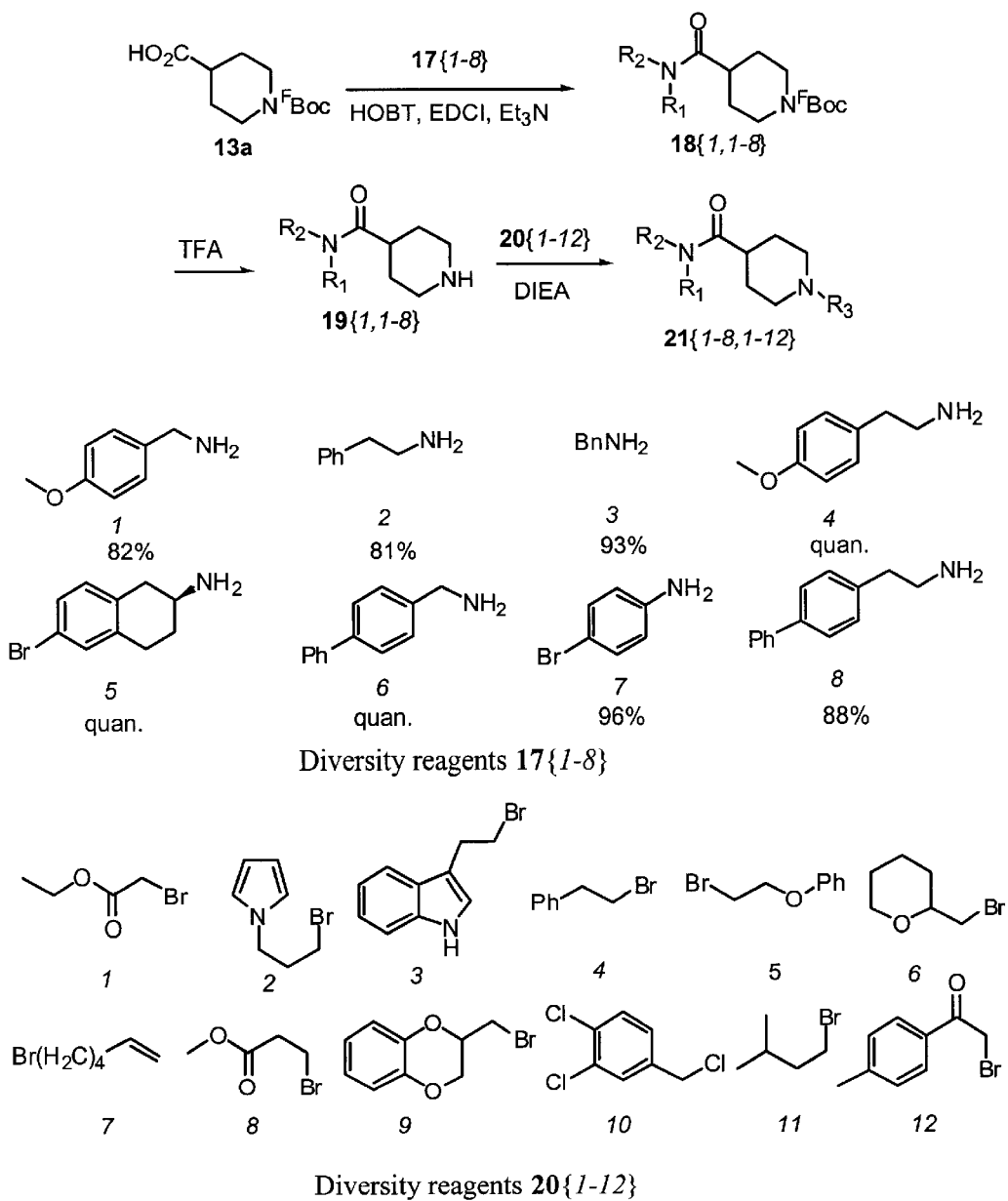
FIG. 8 illustrates the synthesis of the 96-compound library that is described in Example 15.

General Procedure for the Synthesis of the Library in FIGS. 8 and 9

Eight vials were charged with a mixture of acid 13a (330 mg, 0.50 mmol), an amine 17{1–8} (2.0 mmol), EDCI (0.70 mmol), HOBT (0.70 mmol) and triethylamine (0.70 mmol) in chloroform/DMF. The reaction mixtures were stirred at room temperature overnight (16 h) and quenched with water. The organic phase was collected and evaporated with a vacuum centrifuge. These residues were charged onto eight short columns packed with fluorous reverse phase silica gel (5 g, bonded phase—$Si(Me)_2CH_2CH_2C_6F_{13}$). Each column was eluted with 80:20 MeOH—$H_2O$ (15 mL) followed by MeOH (5 mL) and diethyl ether (20 mL). The combined MeOH and ether fractions were evaporated to dryness with a vacuum centrifuge to give library 18{1–8}. A mixture of dichloromethane and TFA (1:1, 5 mL) was added to each of these amides 18. The reaction mixtures were stirred at room temperature for 2.5 h. After removal of dichloromethane and TFA, stock solutions of the residues 19{1–8} were prepared. Each of these eight solutions in DMF was added to an array of twelve halides 20{1–12} in the presence of diisopropylethylamine (0.5 mmol). These 96 reaction mixtures were heated at 50° C. for 48 h. After concentration, the mixtures were purified with a PrepLCMS system. In 89 out of 96 reactions, the desired products were detected by LC-MS and isolated in yields from 5 to 100% (FIG. 9). Spectroscopic data for twelve members of library 21{1–8, 1–12} are listed below.

Compound 21{2,2}. $^1H$ NMR (DMSO-d6) δ 9.3 (br, 2H), 8.04 (t, J=3.3 Hz, 1H), 7.28 (m, 2H), 7.20 (m, 2H), 6.76 (m, 2H), 6.01 (m, 2H), 3.94 (t, J=4.1 Hz, 2H), 3.47 (d, J=7.1 Hz, 2H), 3.28 (q, J=4.0 Hz, 2H), 2.97–2.84 (m, 4H), 2.70 (t, J=4.3 Hz, 2H), 2.32–2.29 (m, 1H), 2.11–2.05 (m, 2H), 1.84–1.71 (m, 4H); $^{13}C$ NMR (DMSO-d6) δ 172.5, 139.4, 128.6, 128.2, 126.1, 120.5, 107.9, 53.6, 51.2, 45.8, 35.0, 25.9, 25.5.

Compound 21{3,7}. ¹H NMR (DMSO-d6) δ 9.21 (br, 1H), 8.50 (t, J=5 Hz, 2H), 7.32 (t, J=4.5 Hz, 2H), 7.24 (t, J=4.5 Hz, 2H), 5.82–5.77 (m, 1H), 5.03 (d, J=10.5 Hz, 1H), 4.98 (d, J=6.1 Hz, 1H), 4.26 (d, J=3.5 Hz, 2H), 3.51 (d, J=7.1 Hz, 2H), 3.05–3.01 (m, 2H), 2.89 (q, J=6.6 Hz, 2H), 2.47–2.44 (m, 1H), 2.05 (q, J=4.3 Hz, 2H) 1.93 (d, J=8.1 Hz, 2H), 1.84–1.79 (m, 2H), 1.67–1.60 (m, 2H), 1.37 (q, J=4.5 Hz, 2H); ¹³C NMR (DMSO-d6) δ 172.7, 139.4, 138.0, 128.3, 127.1, 126.8, 115.3, 55.8, 51.1, 41.9, 32.5, 25.9, 25.2, 22.7.

Compound 21{2,9} ¹H NMR (DMSO-d6) δ 8.03 (s, 1H), 7.30–7.27 (m, 2H), 7.21–7.18 (m, 2H), 6.94–6.89 (m, 5H), 4.7 (s, 1H), 4.29 (dd, J=7.0, 1.1 Hz, 1H), 3.05 (s, 2H), 2.71 (t, J=4.4 Hz, 2H), 2,35 (s, 1H), 1.89 (m, 4H); ¹³C NMR (DMSO-d6) δ 172.5, 139.4, 128.7, 128.3, 126.1, 121.8, 117.4, 117.2, 68.0, 65.0, 55.8, 52.4,.51.7, 35.0, 25.9.

Compound 21{4,4} ¹H NMR (DMSO-d6) δ 9.47 (s, 1H), 8.01 (t, J=3.3 Hz, 1H), 7.37–7.34 (m, 2H), 7.30–7.25 (m, 2H), 7.10 (d, J=5.0 Hz, 2H), 6.84 (d, J=5.0 Hz, 2H), 3.72 (s, 3H), 3.57 (m, 2H), 3.34–3.31 (m, 5H), 3.00–2.84 (m, 4H), 2.64 (t, J=4.4 Hz, 2H), 2.37–2.32 (m, 1H), 1.89–1.73 (m, 3H); ¹³C NMR (DMSO-d6) δ 172.5, 157.7, 136.9, 131.2, 129.7, 128.8, 126.9, 114.1, 113.7, 56.6, 55.1, 51.2, 34.2, 29.5, 25.9.

Compound 21{1,1}. ¹H NMR (DMSO-d6) δ 8.41 (t, J=3.5 Hz, 1H), 7.15 (d, J=5.1 Hz, 2H), 6.88 (d, J=5.1 Hz, 2H), 4.25–4.19 (m, 6H), 3.72 (s, 3H), 3.01 (s, 2H), 1.92 (br, 4H), 1.24 (t, J=4.2 Hz, 3H); ¹³C NMR (DMSO-d6) δ 172.5, 165.9, 158.2, 131.3, 128.5, 113.7, 61.9, 55.1, 41.4, 25.6, 13.9.

Compound 21{6,10}. ¹H NMR (DMSO-d6) δ 8.54 (t, J=3.5 Hz, 1H), 7.78–7.72 (m, 2H), 7.69–7.57 (m, 4H), 7.50–7.44 (m, 3H), 7.37–7.31 (m, 3H), 4.31–4.25 (m, 4H), 3.41 (d, J=7.1 Hz, 2H), 2.99–2.95 (m, 2H), 2.50–2.47 (m, 1H), 1.97–1.80 (m, 4H); ¹³C NMR (DMSO-d6) δ 172.7, 139.9, 138.8, 138.6, 133.3, 132.5, 129.0, 127.8, 126.9, 126.6, 57.7, 50.9, 41.7, 25.8.

Compound 21{5,3}. ¹H NMR (DMSO-d6) δ 11.0 (s, 1H), 10.2 (s, 1H), 7.62–7.57 (m, 3H), 7.51 (d, J=4.5 Hz, 2H), 7.38 (d, J=4.8 Hz, 2H), 7.25 (s, 1H), 7.12–7.09 (m, 1H), 7.04–7.01 (m, 1H), 3.72 (d, J=7.1 Hz, 2H), 3.14–3.11 (m, 2H), 3.03 (q, J=6.7 Hz, 2H), 2.66–2.60 (m, 1H), 2.09–186 (m, 4H); ¹³C NMR (DMSO-d6) δ 171.9, 138.4, 136.3, 131.5, 126.6, 123.2, 121.3, 121.1, 118.5, 118.2, 114.9, 111.6, 108.9, 56.1, 51.0, 25.8, 19.8.

Compound 21{8,12}. ¹H NMR (DMSO-d6) δ 8.05 (s, 1H), 7.87 (d, J=4.5 Hz, 2H), 7.63 (d, J=4.5 Hz, 2H), 7.57 (d, J=4.2 Hz, 2H), 7.47–7.42 (m, 3H), 7.36–7.33 (m, 1H), 7.27 (d, J=4.7 Hz, 2H), 4.98 (s, 4H), 3.52–3.49 (m, 2H), 3.02–3.00 (m, 2H), 2.76 (t, J=4.3 Hz, 2H), 2.39 (s, 3H), 1.90 (br, 4H).

Compound 21{5,11}. ¹H NMR (DMSO-d6) δ 9.2 (s, 1H), 8.04 (d, J=4.5 Hz, 1H), 7.30 (s, 1H), 7.26 (d, J=5.7 Hz, 1H), 7.02 (d, J=5.0 Hz, 1H), 3.93 (s, 1H), 3.51 (d, J=7.2 Hz, 2H), 3.06–3.02 (m, 2H), 2.93–2.78 (m, 4H), 2.56–2.53 (m, 2H), 2.38–2.35 (m, 1H), 1.88–1.76 (m, 5H), 1.64–1.50 (m, 3H), 0.90 (d, J=4.6 Hz, 6H); ¹³C NMR (DMSO-d6) δ 172.3, 138.4, 134.1, 131.2, 130.9, 128.4, 118.6, 54.5, 51.1, 44.3, 34.3, 31.9, 27.9, 26.9, 26.0, 25.9, 25.7, 22.1.

Compound 21{5,5}. ¹H NMR (DMSO-d6) δ 8.04 (d, J=4.5 Hz, 1H), 7.35–7.26 (m, 4H), 7.04–6.99 (m, 4H), 4.33 (t, J=2.8 Hz, 2H), 3.94–3.92 (m, 1H), 3.61 (d, J=7.2 Hz, 2H), 3.57 (s, 2H), 3.04–3.02 (m, 2H), 2.94–2.89 (m, 1H), 2.87–2.78 (m, 2H), 2.56–2.53 (m, 1H), 2.40–2.37 (m, 1H), 1.90–1.84 (m, 4H), 1.64–1.62 (m, 1H); ¹³C NMR (DMSO-d6) δ 172.3, 157.5, 138.4, 134.1, 131.2, 130.9, 129.6, 128.4, 121.4, 118.6, 114.7, 62.0, 55.0, 51.8, 44.3, 34.3, 27.9, 26.9, 25.9.

Compound 21{1,8}. ¹H NMR (DMSO-d6) δ 8.42 (t, J=3.4 Hz, 1H), 7.15 (d, J=5.1 Hz, 2H), 6.87 (d, J=5.2 Hz, 2H), 4.19 (d, J=3.3 Hz, 2H), 3.72 (s, 3H), 2.94 (t, J=6.9 Hz, 2H), 2.84 (t, J=4.5 Hz, 1H), 2.74 (t, J=4.5 Hz, 1H), 2.4 (m, 1H), 1.93–1.77 (m, 4H); ¹³C NMR (DMSO-d6) δ 171.6, 170.6, 169.5, 130.3, 127.5, 112.7, 54.1, 50.9, 50.4, 40.4, 27.7, 27.4, 25.0.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A method of increasing the fluorous nature of an organic compound, including the step of reacting the organic compound with at least one second compound having the formula:

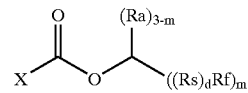

to create a fluorous tagged organic compound, wherein Rf is a fluorous group, Rs is a spacer group, d is 1 or 0, m is 1, 2 or 3, Ra is an alkyl group and X is a leaving group, the organic compound having an amine or an amino functional group reactive with the second compound, the fluorous nature of the fluorous tagged organic compound being increased as compared to the organic compound to enable separation of the fluorous tagged organic compound from at least one other compound by using a fluorous separation technique.

2. The method of claim 1 wherein the leaving group is a halide, —N₃, —CN, RO—, NH₂O—, NHRO—, NR₂O—, RCO₂—, ROCO₂—, RNCO₂—, RS—, RC(S)O—, RCS₂—, RSC(O)S—, RSCS₂— RSCO₂—, ROC(S)O—, ROCS₂—, RSO—, RSO₃—, ROSO₂—, ROSO₃—, RPO₃—, ROPO₃—, an N-imidazolyl group, an N-triazolyl group, an N-benzotriazolyl group, a benzotriazolyloxy group, an imidazolyloxy group, an N-imidazolinone group, an N-imidazolone group, an N-imidazolinethione group, an N-succinimidyl group, an N-phthalimidyl group, an N-succinimidyloxy group, an N-phthalimidyloxy group, —ON=C(CN)R, or a 2-pyridyloxy group, wherein R is an alkyl group or an aryl group.

3. The method of claim 1 wherein Rs is an alkylene group.

4. The method of claim 3 wherein Rs is —CH₂CH₂—.

5. The method of claim 1 wherein Ra is a $C_1$–$C_6$ alkyl group.

6. The method of claim 1 wherein the fluorous group is a perfluorocarbon, a fluorohydrocarbon, a fluorinated ether or a fluorinated amine.

7. The method of claim 1 wherein fluorous group is a perfluoroalkyl group.

* * * * *